(12) United States Patent  (10) Patent No.: US 8,137,109 B2
Gatzemeyer et al.  (45) Date of Patent: Mar. 20, 2012

(54) INTERACTIVE ORAL CARE IMPLEMENT SYSTEM

(75) Inventors: John J. Gatzemeyer, Hillsborough, NJ (US); Eduardo J. Jimenez, Manalapan, NJ (US); Robert Riebe, Minneapolis, MN (US); Paul Fair, Denver, CO (US); Dong Ho Yun, Bayside, NY (US)

(73) Assignee: Colgate-Palmolive Company, New York, NY (US)

( * ) Notice: Subject to any disclaimer, the term of this patent is extended or adjusted under 35 U.S.C. 154(b) by 366 days.

(21) Appl. No.: 11/859,327

(22) Filed: Sep. 21, 2007

(65) Prior Publication Data

US 2008/0141478 A1   Jun. 19, 2008

Related U.S. Application Data

(63) Continuation-in-part of application No. 11/610,248, filed on Dec. 13, 2006.

(51) Int. Cl.
  *G09B 19/00* (2006.01)
  *A63F 13/00* (2006.01)
  *A46B 15/00* (2006.01)

(52) U.S. Cl. ........ 434/238; 434/118; 434/236; 434/308; 463/1; 15/105

(58) Field of Classification Search .................. 434/238; 15/105; 463/1
  See application file for complete search history.

(56) References Cited

U.S. PATENT DOCUMENTS

| | | | |
|---|---|---|---|
| 4,207,087 A | 6/1980 | Morrison | |
| 5,232,370 A | 8/1993 | Hoye | |
| 5,673,451 A | 10/1997 | Moore et al. | |
| 5,810,601 A | 9/1998 | Williams | |
| 5,864,288 A * | 1/1999 | Hogan | 340/568.1 |
| 5,875,796 A | 3/1999 | Silver-Isenstadt et al. | |
| 5,924,159 A | 7/1999 | Haitin | |
| 5,930,858 A | 8/1999 | Jung | |
| 5,943,723 A * | 8/1999 | Hilfinger et al. | 15/22.1 |
| 5,944,531 A * | 8/1999 | Foley et al. | 434/263 |
| 6,154,912 A | 12/2000 | Li | |
| 6,199,239 B1 | 3/2001 | Dickerson | |
| 6,202,242 B1 | 3/2001 | Salmon et al. | |
| 6,389,633 B1 | 5/2002 | Rosen | |

(Continued)

FOREIGN PATENT DOCUMENTS

CA   2 232 528 A1   9/1999

(Continued)

OTHER PUBLICATIONS

International Search Report of PCT/US2007/087134, Mar. 25, 2008.

(Continued)

*Primary Examiner* — Kang Hu

(74) *Attorney, Agent, or Firm* — Amy M. Fernandez

(57) ABSTRACT

An oral care implement has a user-interactive display that displays images representing oral care regions of the mouth. The user can interact with the display by playing a game, which can relate to oral care. An oral care implement has a plurality of lighted segments that can be sequentially illuminated to indicate a recommended brushing sequence. The lighted segments can be shaped and/or labeled to indicate particular oral care regions of the mouth. In accordance with another aspect, an oral care implement can be equipped with features to encourage social interaction between two or more individuals.

11 Claims, 16 Drawing Sheets

U.S. PATENT DOCUMENTS

| | | | |
|---|---|---|---|
| 6,442,787 | B2 | 9/2002 | Hohlbein |
| 6,461,238 | B1 | 10/2002 | Rehkemper et al. |
| 6,536,068 | B1 * | 3/2003 | Yang et al. .................. 15/105 |
| 6,611,780 | B2 * | 8/2003 | Lundell et al. ............... 702/122 |
| 6,731,213 | B1 * | 5/2004 | Smith ....................... 340/573.1 |
| 6,754,928 | B1 * | 6/2004 | Rosen ........................... 15/105 |
| 6,802,097 | B2 | 10/2004 | Hafliger et al. |
| 6,850,167 | B2 | 2/2005 | Rosen |
| 6,954,961 | B2 * | 10/2005 | Ferber et al. ................. 15/22.1 |
| 7,003,839 | B2 | 2/2006 | Hafliger et al. |
| 7,448,109 | B2 | 11/2008 | Brewer et al. |
| 2001/0034917 | A1 | 11/2001 | DuCey |
| 2003/0017874 | A1 * | 1/2003 | Jianfei et al. ................... 463/46 |
| 2003/0063011 | A1 | 4/2003 | Rosen |
| 2003/0115694 | A1 | 6/2003 | Pace |
| 2003/0205492 | A1 | 11/2003 | Ferber et al. |
| 2004/0134000 | A1 | 7/2004 | Hilfinger et al. |
| 2005/0091769 | A1 | 5/2005 | Jimenez |
| 2005/0229345 | A1 * | 10/2005 | Rouse et al. .................... 15/105 |
| 2006/0037158 | A1 * | 2/2006 | Foley et al. .................... 15/105 |
| 2006/0040246 | A1 * | 2/2006 | Ding et al. ...................... 434/263 |
| 2006/0117508 | A1 | 6/2006 | Hohlbein |
| 2006/0257822 | A1 * | 11/2006 | Ghosh et al. .................. 433/215 |
| 2007/0094822 | A1 | 5/2007 | Gatzemeyer |
| 2007/0136964 | A1 * | 6/2007 | Dawley ......................... 15/22.1 |
| 2007/0270221 | A1 * | 11/2007 | Park et al. ....................... 463/37 |
| 2008/0109973 | A1 | 5/2008 | Farrell et al. |
| 2009/0143914 | A1 | 6/2009 | Cook et al. |

FOREIGN PATENT DOCUMENTS

| | | |
|---|---|---|
| CN | 2299526 | 12/1998 |
| CN | 1416759 | 5/2003 |
| CN | 2633244 | 8/2004 |
| CN | ZL 200420014704.6 | 3/2005 |
| DE | 3935554 | 5/1991 |
| DE | 4029770 | 3/1992 |
| DE | 195 06 129 A1 | 8/1996 |
| DE | 299 15 858 U1 | 9/1999 |
| DE | 10001502 A1 | 3/2001 |
| DE | 100 26 513 A1 | 5/2001 |
| DE | 100 45 353 A1 | 3/2002 |
| DE | 10120090 | 8/2002 |
| DE | 101 54 946 A1 | 5/2003 |
| DE | 10247698 | 4/2004 |
| DE | 102006005205 A1 | 9/2006 |
| FR | 2544602 | 10/1984 |
| FR | 2724298 | 3/1996 |
| JP | 8-19427 A | 1/1996 |
| JP | 2003310644 | 11/2003 |
| JP | 2002369718 | 12/2005 |
| RU | 2098993 | 12/1997 |
| RU | 2174381 | 10/2001 |
| WO | 2006/065159 A2 | 6/2006 |
| WO | 2006137648 A | 12/2006 |
| WO | WO 2007/072430 | 6/2007 |
| WO | WO 2007/097886 | 8/2007 |

OTHER PUBLICATIONS

International Search Report for PCT/US2008/053909 filed Feb. 14, 2008 Dated Jul. 3, 2008.

Examiner's First Report from the Patent Office of Australia for corresponding Australian Patent Application No. 2008216204 dated Sep. 23, 2010.

Search Report from the Intellectual Property Office of Taiwan for corresponding Tawian Patent Application No. 097105282 dated Jan. 26, 2011.

Examination Report from the National Office of Intellectual Property of Vietnam for corresponding Vietnamese Patent Application No. 1-2009-01946 dated Mar. 23, 2011.

* cited by examiner

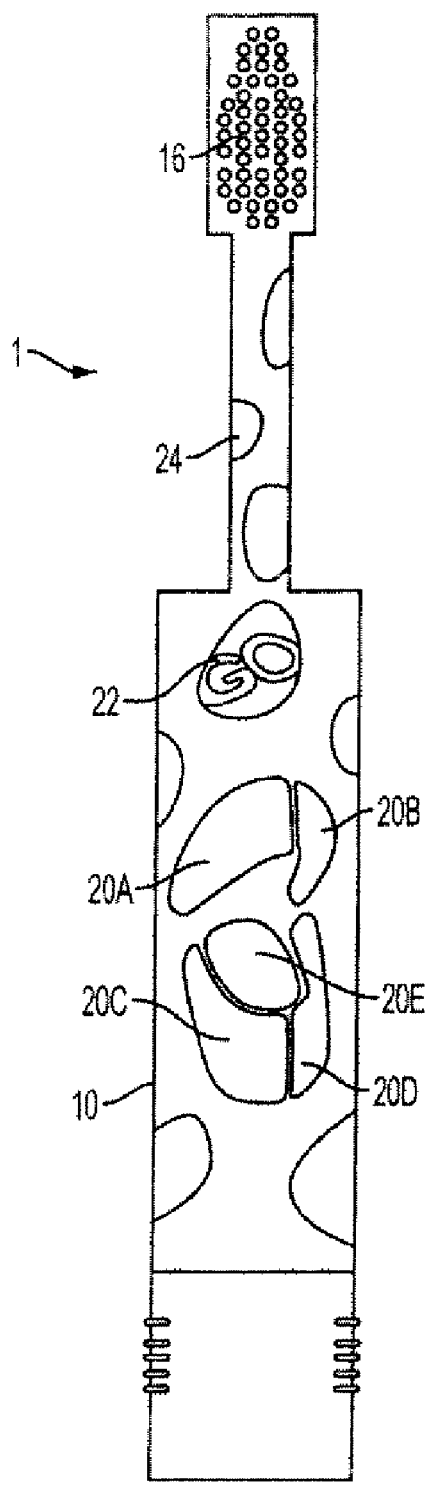
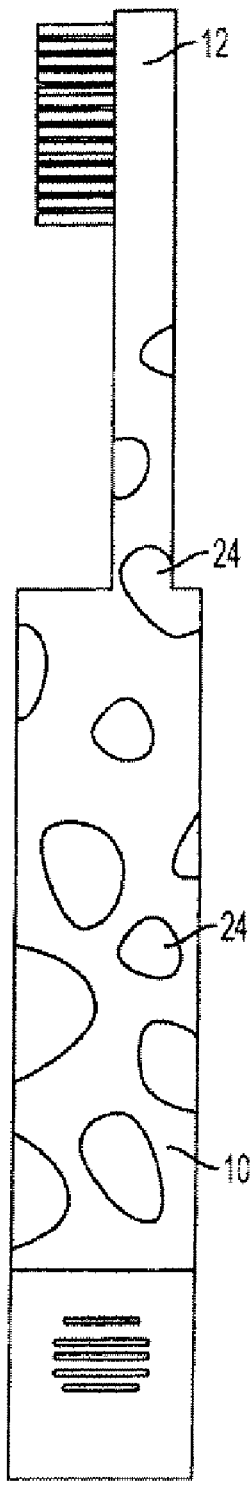
FIG. 1A
FIG. 1B

INTERACTIVE ORAL CARE IMPLEMENT SYSTEM

CROSS REFERENCE TO RELATED APPLICATIONS

This application is a continuation-in-part of application Ser. No. 11/610,248, filed Dec. 13, 2006, the disclosure of which is hereby incorporated by reference.

FIELD OF THE INVENTION

The present invention pertains to an oral care implement, in particular to a toothbrush for providing an interactive competition between users of toothbrushes.

BACKGROUND OF THE INVENTION

Dentists generally recommend that an individual brush his or her teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects.

BRIEF SUMMARY OF THE INVENTION

An oral care implement, such as a toothbrush, provides an entertaining and/or educational interactive competition for the user to promote oral hygiene.

The entertaining and/or educational environment can be provided by enabling a user/player to brush his teeth and interact with a computer implemented game on a toothbrush. In one embodiment, an oral care implement provides for a synergistic combination of education and entertainment for games pertaining to oral care hygiene. Indeed, an educational game directed to oral care can be more entertaining and more educational than simple instructions. This is because, in one aspect, a player is provided with an interactive reward in which the virtual elements performing the educational functions form the basis of an interactive computer game for the player/user.

According to one aspect, an oral care implement includes a plurality of lighted segments for indicating two or more oral care regions of the mouth. The oral care implement also has a processor for causing the segments to be sequentially lighted for prescribed intervals. The segments can be used to instruct a user to brush in a particular oral care region during the prescribed interval.

In another aspect, an oral care implement has a display for displaying images associated with oral care regions of the mouth, and an input device for interacting with the images. The images can be sequentially displayed to instruct the user to brush in particular oral care regions during sequential intervals. The user can interact with the images by playing a game or the like.

In another aspect, an oral care implement comprises a processor, a display, and a memory for storing instructions. When executed by the processor, the memory causes the oral care implement to sequentially display graphical objects at prescribed intervals, and enable user interaction with the graphical objects. The user can interact with the graphical objects by playing a game or the like.

In yet another aspect, an oral care implement comprises a display for displaying graphical objects associated with oral care. The graphical objects collectively define a computer implemented process for oral care gaming. The oral care implement also has an input device to allow a user to interact with the computer implemented process.

In another aspect, an oral care implement comprises a processor, a display, and a memory for storing instructions. When executed by the processor, the memory causes the oral care implement to sequentially display text at prescribed intervals and display graphical objects. The memory also enables user interaction with the graphical objects.

In accordance with another aspect, an oral care implement includes a body for gripping the implement; and the body includes at least one of a display and an audio speaker. The oral care implement is adapted to communicate with another oral care implement via a data connection for selectively activating the display or speaker.

In another aspect, an oral care implement can be equipped with features to encourage social interaction between two or more individuals that can help promote good oral care habits. By encouraging social interaction between individuals, such as children, the overall oral care experience can be made more positive. For example, two or more oral care implements can be provided with user input devices and light displays and/or audio speakers and adapted to communicate with each other to enable two or more individuals to play a game against each other.

Other features and advantages of the invention will become apparent from the following description taken in conjunction with the following drawings.

BRIEF DESCRIPTION OF THE DRAWINGS

FIG. 1A is a front view of a toothbrush to according to one or more aspects of an illustrative construction;

FIG. 1B is a side view of the toothbrush of FIG. 1A;

DETAILED DESCRIPTION OF THE INVENTION

Figure 2A:
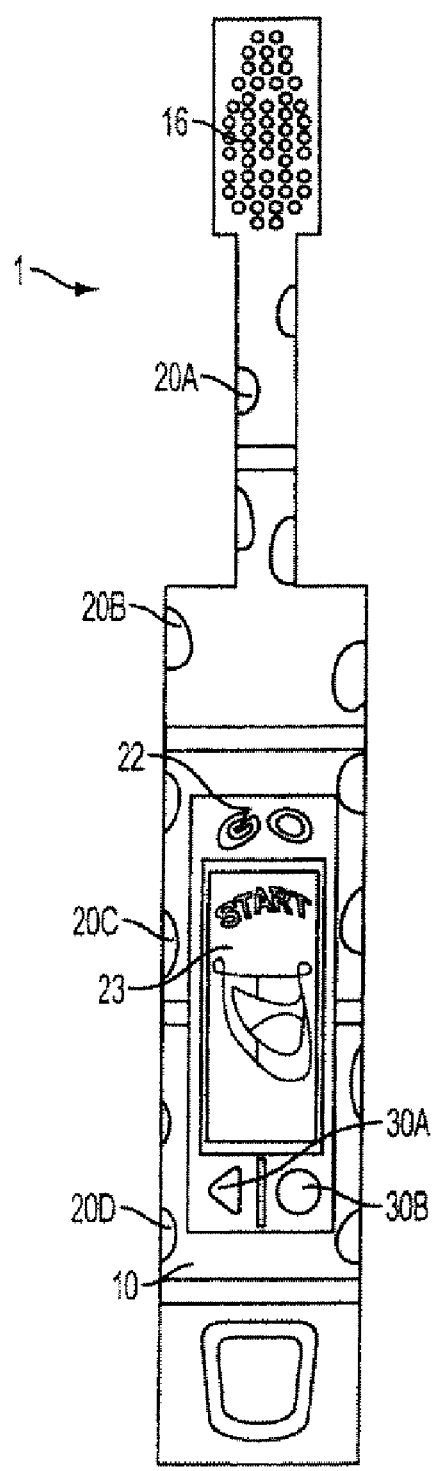
FIG. 2A is a front view of an alternative toothbrush to according to one or more aspects of an illustrative construction.

FIGS. 1A and 1B illustrate a toothbrush 1 having a body, such as a handle 10 and a head 12 containing tooth cleaning elements, such as bristles 16 and/or elastomeric cleaning elements (not shown). Any bristle configuration and any handle configuration can be used, and the present invention should not be regarded as being limited to any particular configuration. Toothbrushes described and shown in other embodiments below may share these features and such description will not be repeated, with like reference numerals corresponding to like elements. The toothbrush may be manual or powered for moving/oscillating the tooth cleaning elements of the head 12.

The head 12 may be integral with or permanently attached to the handle 10, or may be replaceable. One or more other oral surface engaging elements, such as a flossing element, plaque scrapper, elastomeric massaging elements, and the like, may also be present on the toothbrush 1. In practice, the toothbrush can have any of these features alone or in any combination with other features not illustrated herein. The bristles 16 generally extend from the surface of head 12 and can be of conventional size and spacing. It will also be appreciated that while the cleaning elements are illustrated herein as tufts of bristles 16, other cleaning elements of varying size, shape, cross-section and material may be used.

In the embodiment shown in FIGS. 1A and 1B, the toothbrush 1 includes a plurality of lighted segments 20A-20E, which together represent tooth quadrants and a tongue. A button 22 is provided to enable a user to activate the functionality of the toothbrush, as described below. The toothbrush 1 optionally may include a plurality of additional lighted areas 24 at various locations on the handle 10. The lighted areas 24 may be uniformly sized and spaced or, as shown in FIGS. 1A and 1B, may be differently sized and/or spaced if desired. The button 22 may be similar in appearance to the lighted areas 24 and optionally may be lighted. Alternatively, some or all of areas 24 may be decorative only instead of being lighted.

The lighted segments 20A-20E may together represent an open mouth, with four generally quarter-circle shaped portions 20A-20D resembling groups of teeth surrounding a generally teardrop shaped portion 20E resembling a tongue, as illustrated in FIG. 1A. An internal memory can be configured so that when a user depresses button 22, one or more of the segments is illuminated to instruct the user to brush in a particular brushing zone for a prescribed interval of time. Additional segments thereafter can be sequentially illuminated to instruct the user to brush in additional brushing zones. A suitable interval of time can be selected for each zone, e.g., about 30 seconds. The interval for a zone can be the same or different from the interval for other zone(s).

For example, segments 20B and 20D can be illuminated during a first 30-second interval to instruct the user to brush the outside surfaces of the top and bottom teeth, including the front and back teeth. At the conclusion of the first interval, a second 30-second interval begins during which segment 20C may be illuminated to instruct the user to brush the upper molars. At the conclusion of the second interval, segment 20A may be illuminated during a third 30-second interval to instruct the user to brush the lower molars. During a fourth 30-second interval, segment 20E may be illuminated to instruct the user to brush the tongue and the surfaces behind the teeth. A four-interval brushing cycle is described merely as exemplary. If desired, a different number of intervals may be chosen, such as two (e.g., upper teeth/lower teeth), three (e.g., front teeth/upper teeth/lower teeth), five (e.g., outside teeth/upper molars/lower molars/back surfaces/tongue), and so on.

After the user has completed brushing in the prescribed brushing zones, some or all of the lighted areas 20A-20E, 22, and 24 can be illuminated, e.g., flashed in a random sequence. The memory can be programmed to cause such lighting for a prescribed interval of time, e.g., 15-20 seconds, as a signal that the user has completed the recommended brushing program. A young child will be encouraged to complete the entire brushing program to receive the reward of this "light show."

Figure 2B:
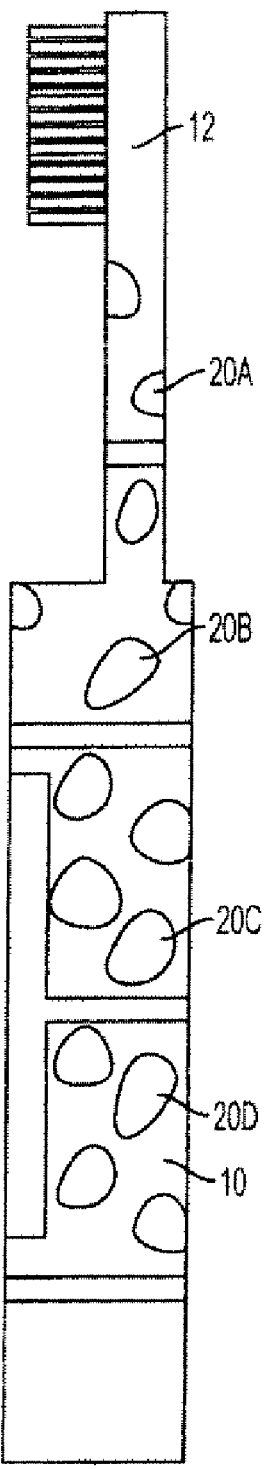
FIG. 2B is a side view of the toothbrush of FIG. 2A.

FIGS. 2A and 2B illustrate another embodiment in which the toothbrush is divided into a plurality of sections each having a plurality of lighted areas 20A, 20B, 20C, and 20D. A display screen 23 is provided for displaying graphical objects. For example, when button 22 is depressed, the display screen can display "start" and a graphical object representing teeth and a tongue, with a portion of the teeth shaded as an instruction to brush the outside surfaces of the upper and lower teeth for a prescribed interval. The display 23 also may display a timer that displays the amount of time remaining in the interval, e.g., in seconds. During the interval, lighted areas 20D in one of the sections are caused to blink as an additional indicator of the current brushing zone. At the conclusion of the interval, a graphical object representing a subsequent brushing zone, e.g., front teeth, can be displayed while lighted areas 20C in another section are caused to blink. This procedure can be repeated for additional brushing zones, e.g., upper molars, lower molars, etc., by displaying a representative object on the display screen 23 and illuminating the lighted areas 20B, 20A, etc. in one of the sections.

At the conclusion of the prescribed brushing intervals, all of the lighted areas 20A-20D can be caused to blink, if desired, as a signal that brushing has been completed. The display can then be caused to display a game, with which the user can interact via controls 30A and 30B. As discussed more fully below, the game can utilize some or all of the objects displayed during brushing. For example, the user may control a "gunship" that fires shots to remove plaque from teeth. The controls 30A and 30B can be used to move the gunship left and right and to fire shots, for example. A variety of structures can be used for the controls 30A and 30B; non-limiting examples include buttons, joysticks, light sensors, touch sensitive surfaces, and combinations thereof.

As a variation of the "gunship" game, the display can be configured so that simulated plaque pieces descend from the top of the screen (e.g., which can be oriented vertically) at random lateral positions. Rectangles representing teeth are displayed across the bottom of the screen. The player controls lateral movement of a toothbrush positioned above the teeth. The object of the game is to position the toothbrush below a descending plaque piece to intercept it before it falls onto a tooth. When a plaque piece is successfully intercepted, it disappears and the player then attempts to intercept subsequent plaque pieces. The velocity and/or frequency of the falling plaque pieces can be made to increase as the game progresses to make the game more challenging the longer it is played. The game can end, for example, when a predetermined number of plaque pieces fall onto a tooth.

Figure 3A:
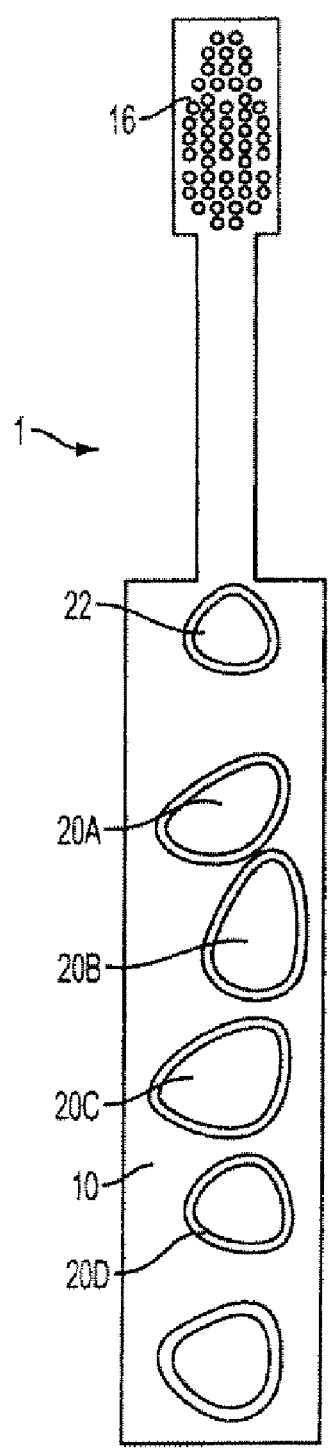
FIG. 3A is a front view of an alternative toothbrush to according to one or more aspects of an illustrative construction.
Figure 3B:
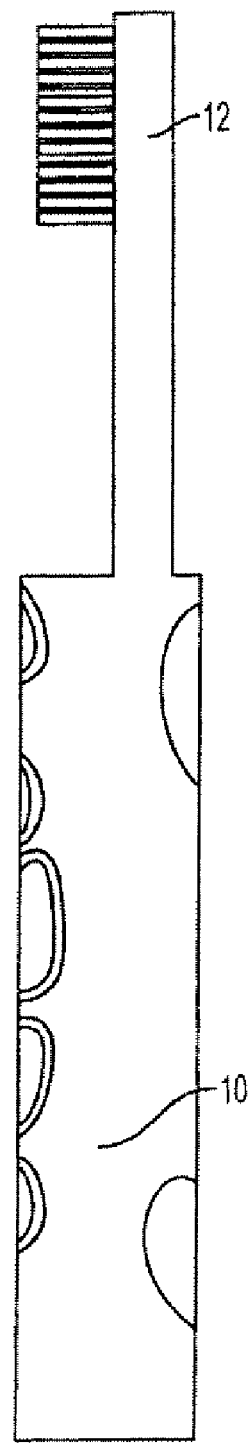
FIG. 3B is a side view of the toothbrush of FIG. 3A.

FIGS. 3A and 3B illustrate an alternative embodiment in which lighted buttons 20A, 20B, 20C, and 20D are provided as indicators of a plurality of brushing zones, e.g., front teeth, upper molars, lower molars, and tongue. After button 22 is depressed, the lighted buttons 20A, 20B, 20C, and 20D are successively caused to be illuminated for respective brushing intervals, e.g., 30-second intervals. At the conclusion of the brushing intervals, the lighted buttons 20A, 20B, 20C, and 20D can be used for a memory game. For example, two or more of the lighted buttons 20A, 20B, 20C, and 20D can be blinked in succession. The object of the game is for the player to repeat the lighting sequence. If the player correctly repeats the lighting sequence, an audible message can be played, such as "good job," and a more complex (e.g., longer sequence) of buttons 20A, 20B, 20C, and 20D can be blinked for the next round. If the player does not correctly repeat a lighting sequence, the player may be given an additional opportunity to repeat the same sequence. Optionally, an incorrectly entered sequence can be indicated in some manner, such as by flashing all of the lighted buttons 20A, 20B, 20C, and 20D together, before the sequence is repeated. Optionally, the game can end after one incorrect sequence (or alternatively two or more consecutive incorrect sequences) are entered.

Figure 4A:
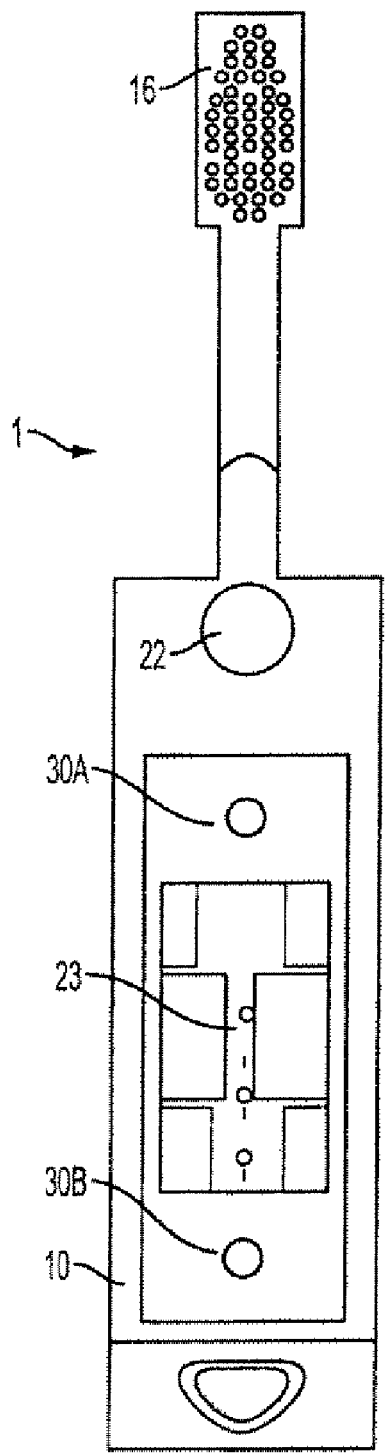
FIG. 4A is a front view of an alternative toothbrush to according to one or more aspects of an illustrative construction.
Figure 4B:
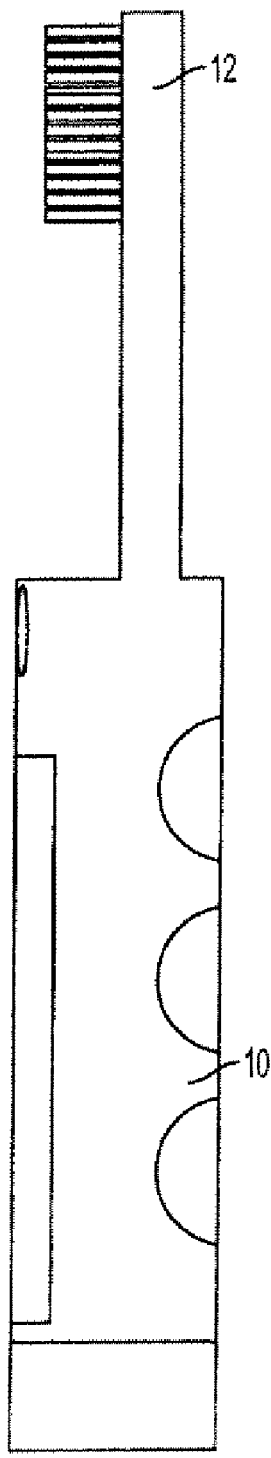
FIG. 4B is a side view of the toothbrush of FIG. 4A.

FIGS. 4A and 4B illustrate another embodiment of a toothbrush 1 having a display screen 23 and game controllers 30A, 30B. The display screen includes six generally rectangular shaped areas representative of tooth sections. Brushing intervals can be indicated by illuminating two or more of the rectangular shaped areas at a time, e.g., to indicate front teeth, upper molars, lower molars, etc. When the user depresses button 22, the display screen 23 displays an indication of the current brushing zone for a prescribed interval. At the conclusion of the brushing intervals, the display screen 23 can display a game, which can include the same graphical objects used during the brushing intervals. For example, the player can control a simulated gun character that shoots plaque off of teeth. In this way, incorporating educational oral care concepts into virtual graphical entities (e.g., simulated teeth and plaque) that the player can battle has the effect of making the gameplay more engaging and entertaining to promote good brushing habits.

Figure 5A:
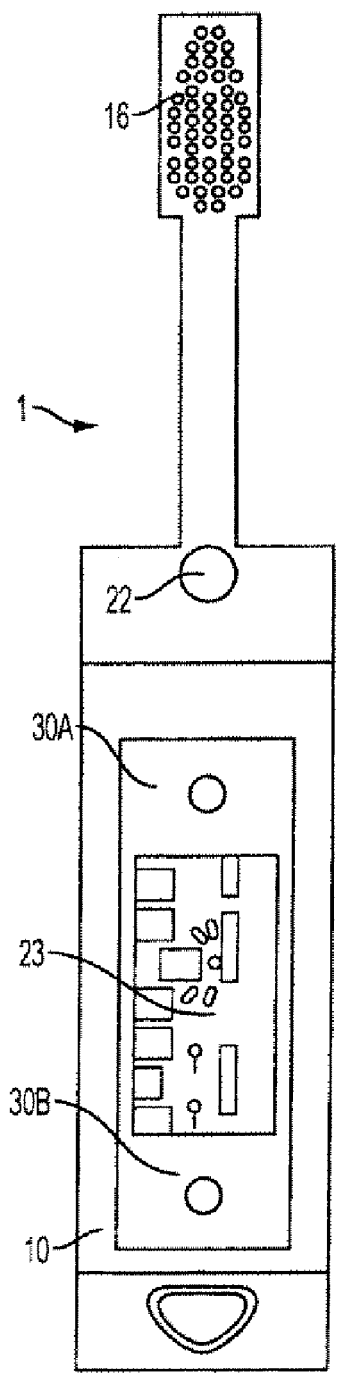
FIG. 5A is a front view of another toothbrush to according to one or more aspects of an illustrative construction.
Figure 5B:
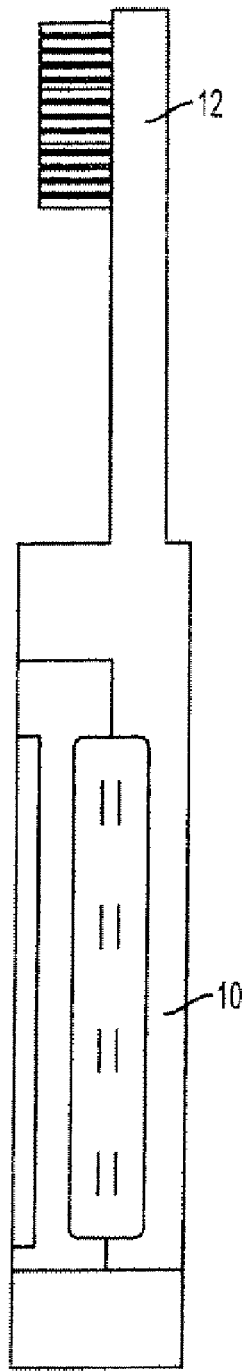
FIG. 5B is a side view of the toothbrush of FIG. 5A.
Figure 5C:
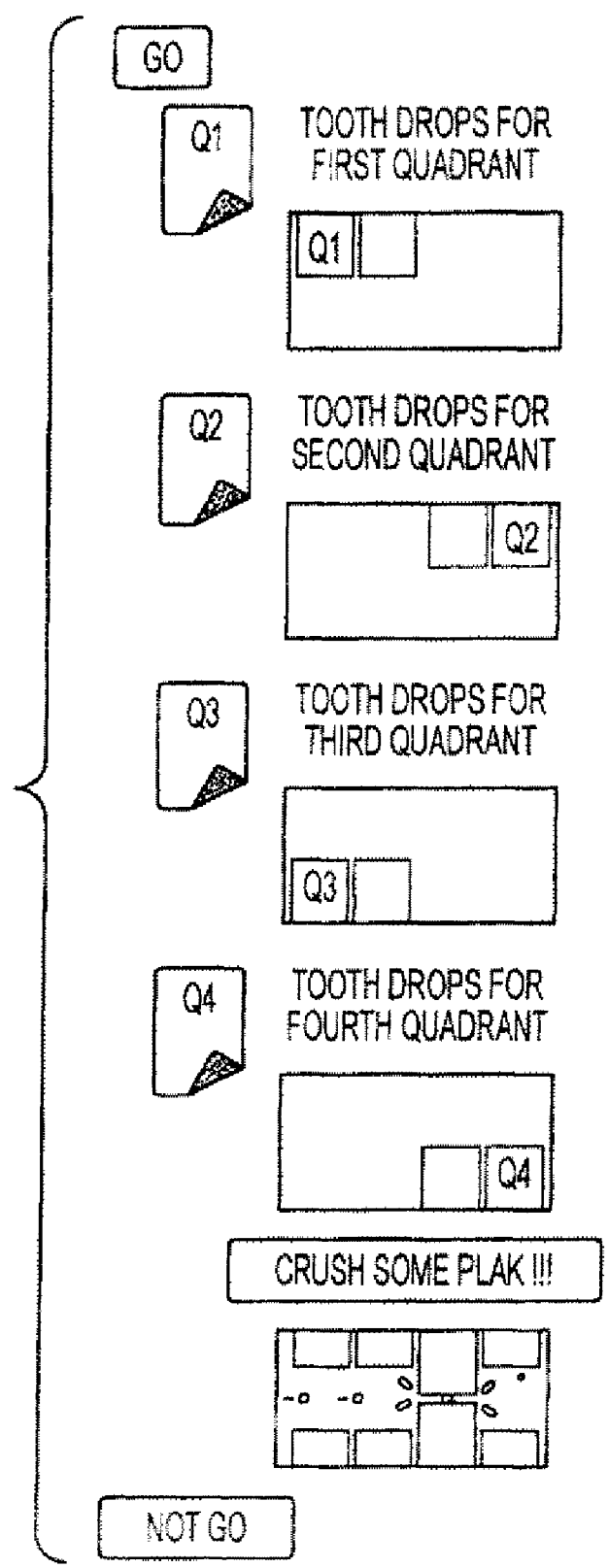
FIG. 5C is a schematic illustration of objects displayed during tooth brushing.

FIGS. 5A and 5B illustrate an alternative embodiment in which the brushing zones are indicated by graphical objects at different locations on the display screen 23. As shown in FIG. 5C, for example, during a first interval two rectangles can be displayed in the upper left corner of the display screen 23 to represent a first brushing zone, e.g., front teeth. Successive intervals are indicated by displaying similar rectangles in the upper right, lower left, and lower right corners of the display screen 23. At the conclusion of brushing, the display screen 23 displays a game, which can include the same graphical objects used during the brushing intervals. For example, the player can select a set of upper and lower "teeth" using one controller 30A, and use another controller 30B to cause the selected "teeth" to converge in an attempt to trap an object (e.g., simulating plaque) therebetween. In this way, incorporating educational oral care concepts into virtual graphical entities that the player can control has the effect of making the gameplay more engaging and entertaining to promote good oral hygiene habits.

Figure 6A:
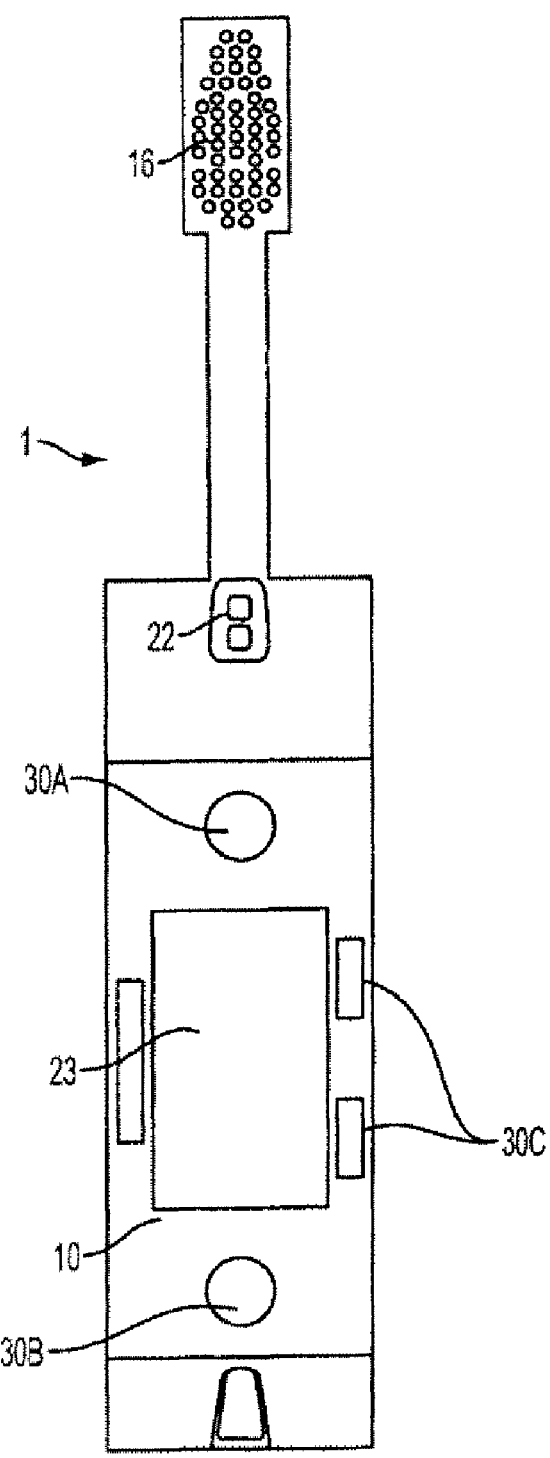
FIG. 6A is a front view of another toothbrush to according to one or more aspects of an illustrative construction.
Figure 6B:
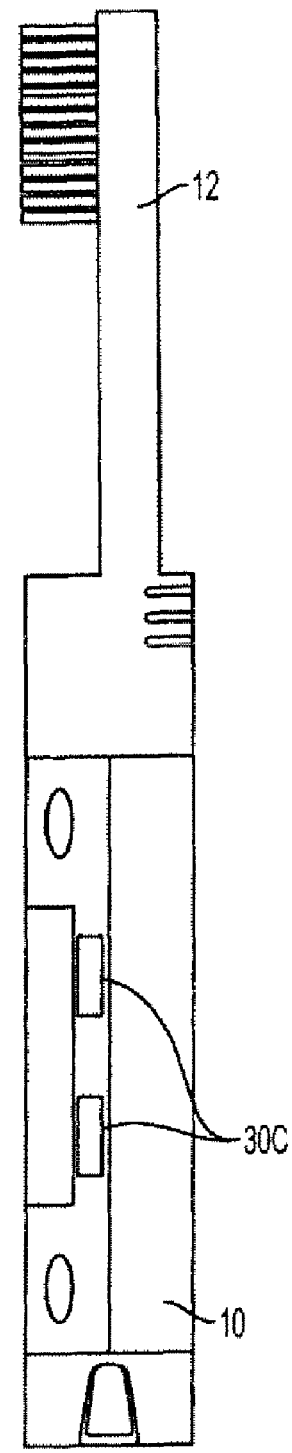
FIG. 6B is a side view of the toothbrush of FIG. 6A.
Figure 6C:
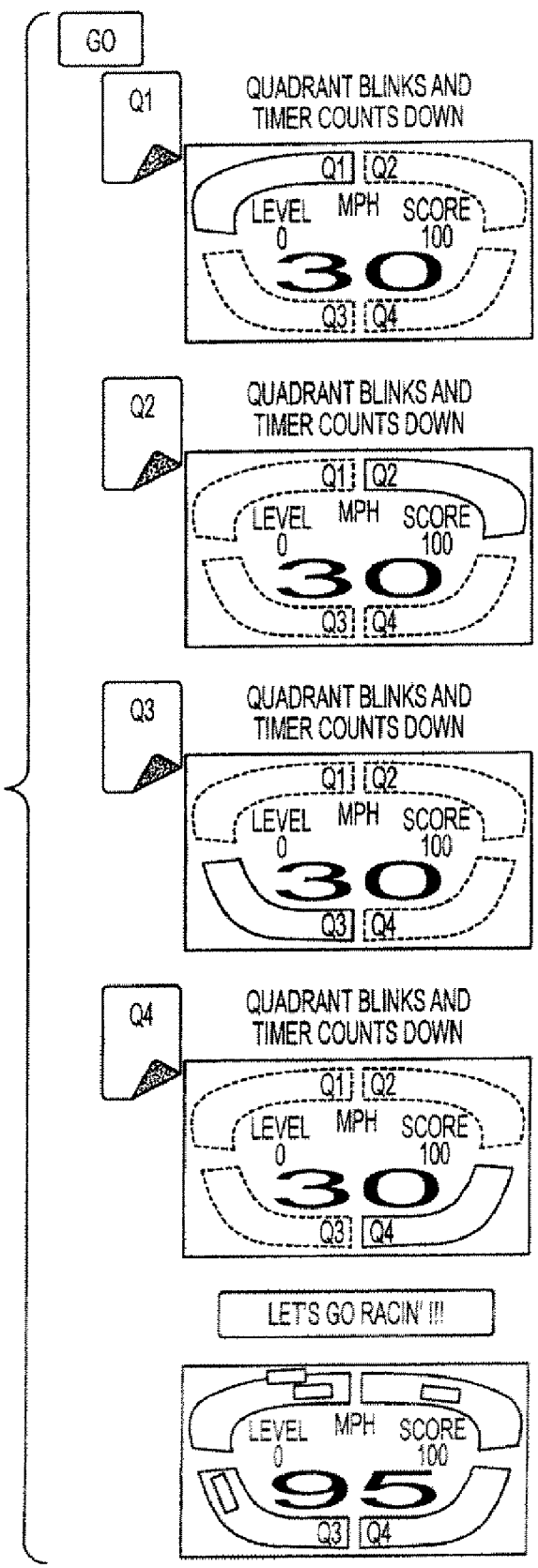
FIG. 6C is a schematic illustration of objects displayed during a tooth brushing process.

In the embodiment illustrated in FIGS. 6A-6C, a display screen 23 includes four quadrants around its periphery (see FIG. 6C) to indicate four brushing zones. The center portion of the display can be used to display the time (e.g., seconds) remaining in the brushing interval. At the conclusion of brushing, the display can be converted into a game, for example, in which the peripheral quadrants are together used as a racetrack around which cars race. The player can control the motion of the car using controls 30A and 30B. Additional game controls 30C optionally can be provided, or areas 30C optionally can be molded as non-functional decorative detail.

Figure 7A:
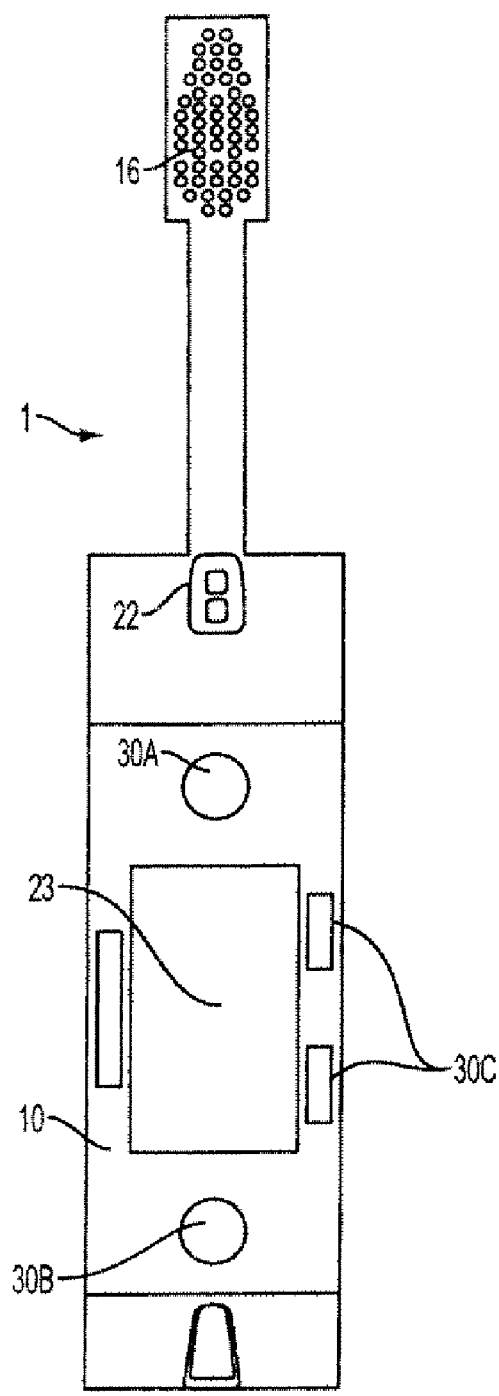
FIG. 7A is a front view of another toothbrush to according to one or more aspects of an illustrative construction.
Figure 7B:
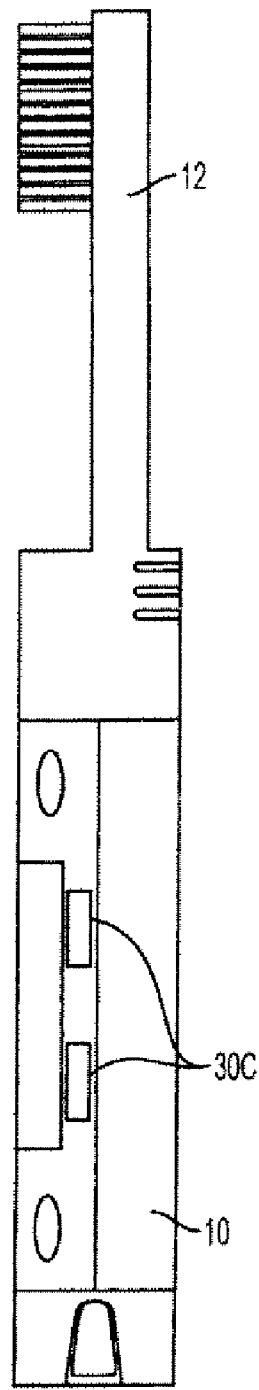
FIG. 7B is a side view of the toothbrush of FIG. 7A.
Figure 7C:
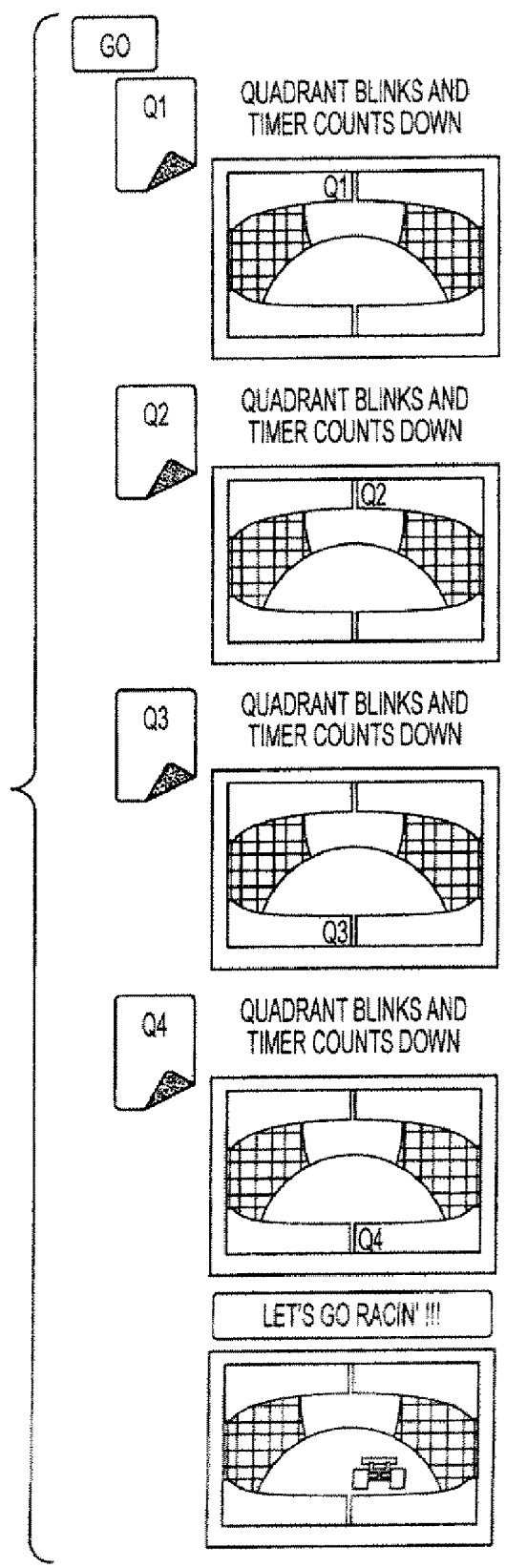
FIG. 7C is a schematic illustration of objects displayed during tooth brushing.

FIGS. 7A-7C illustrate an alternative embodiment in which four peripheral quadrants on the display screen 23 simulate groups of teeth, and a semicircular shaped object representative of a tongue. During brushing, the display screen 23 may display a timer indicating the time remaining in each brushing zone as well as an indicator in the quadrant representative of the current brushing zone. At the conclusion of brushing, the display screen 23 can display a race car, which the player controls via controllers 30A, 30B, and optionally 30C. The game can utilize some or all of the same graphical objects displayed during brushing.

Figure 8A:
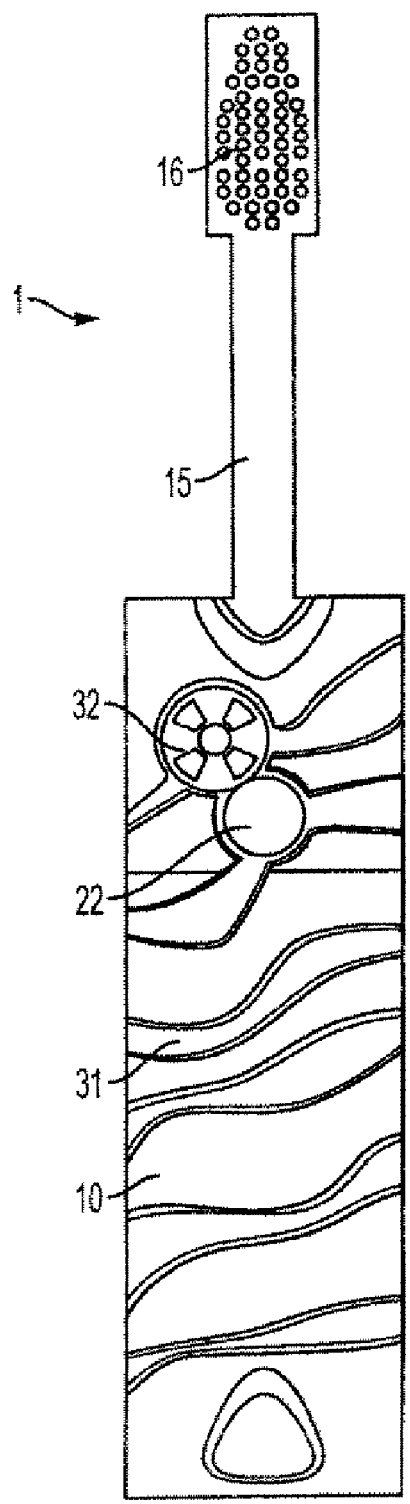
FIG. 8A is a front view of yet another toothbrush to according to one or more aspects of an illustrative construction.
Figure 8B:
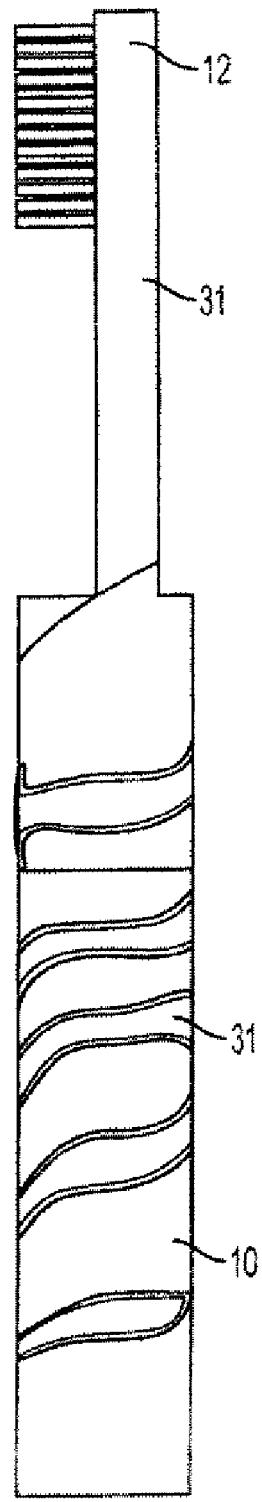
FIG. 8B is a side view of the toothbrush of FIG. 8A.

FIGS. 8A and 8B show another embodiment of a toothbrush 1 having a translucent neck portion 15, in which a plurality of differently colored light emitting diodes (LEDs) are provided. After the user depresses button 22, successive brushing zones are indicated by illuminating one of the LEDs (e.g., 30 seconds blue, 30 seconds red, 30 seconds green, then 30 seconds pink). At the conclusion of brushing, the LEDs can be illuminated in a random sequence, for example, to signal that brushing has been completed. Optionally, a speaker 32 may provide voice instructions during the respective intervals (e.g., "start brushing," "brush front teeth," "brush upper molars," etc.). At the conclusion of brushing, the speaker can play music or give a congratulatory message.

Figure 9A:
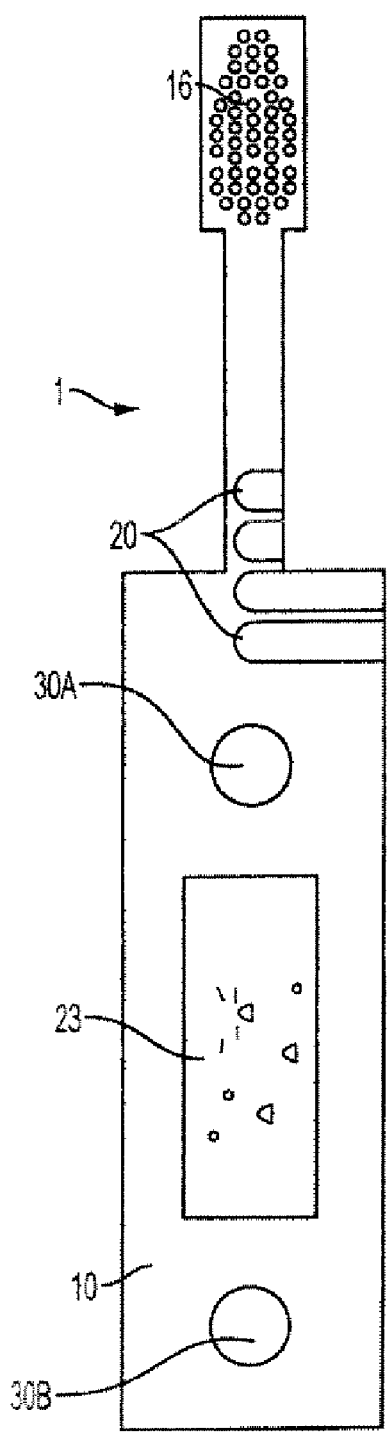
FIG. 9A is a front view of another toothbrush to according to one or more aspects of an illustrative construction.
Figure 9B:
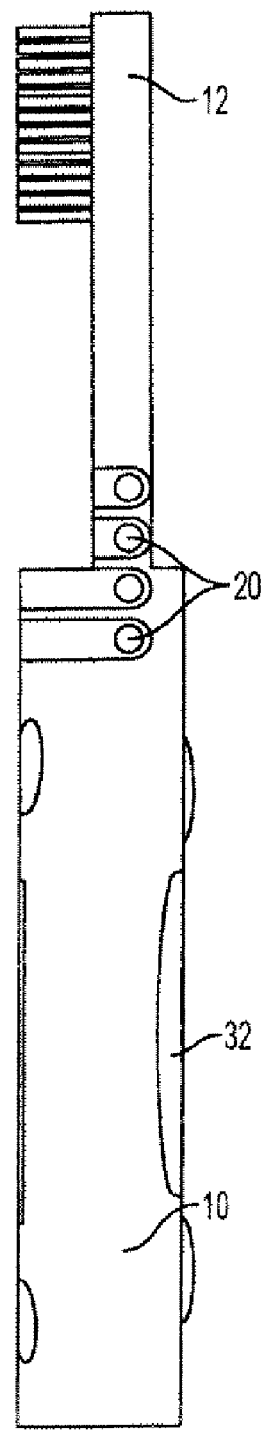
FIG. 9B is a side view of the toothbrush of FIG. 9A.

FIGS. 9A and 9B show an alternative embodiment having a plurality of indicator lights 20 that are illuminated during respective intervals for sequential brushing zones. A display screen 23 can be used to display text for each of the brushing zones (e.g., "front teeth," "upper molars," etc.) during the respective interval. The indicator lights 20 can blink randomly at the conclusion of brushing to signal that brushing has been completed. Following brushing, the display screen 23 can be used to display a game that the player controls via controllers 30A and 30B.

Optionally, the toothbrush 1 may include a motion sensor. A logic circuit can be programmed to shut power off, pause a timer, or take other suitable action in the event the toothbrush is not oscillated in a brushing motion for more than a threshold period of time, e.g., 3-5 seconds. This can help prevent a child from merely watching the light displays or playing the games without actually brushing his or her teeth. In addition, a motion sensor can help preserve battery life by automatically shutting power off when the toothbrush is not in use.

The toothbrush 1 may have a speaker and a suitable audio driver. An audible signal can announce the brushing zone. This may be particularly desirable in embodiments where the visual display(s) are not as easily seen by the user while brushing. The audible signal can be a sound such as beep or chime, which may or may not be distinct for each brushing zone, or may be a voice that announces a brushing zone ("start brushing," "brush front teeth," "brush upper molars," "brush lower molars," "brush tongue," "done," etc.). Optionally, the toothbrush may have mute button to toggle sound on and off.

As described above, the games can utilize the graphic objects or images used during the brushing intervals, e.g., images or objects representing or depicting the mouth, teeth, gums, tongue, etc. Such games can encourage good oral hygiene, for example, where an object of the game is to remove plaque from teeth. In addition, having a mouth, teeth, or the like as scenery or, background in a game can help draw attention to the user's teeth and the need for good oral care.

A wide variety of games can be programmed. For example, an "electronic pet" such as a Tamagotchi® pet or NeoPet® can be programmed. Generally, the game requires the user to "feed" the pet, which enables the pet to evolve into a wide range of characters, depending on how well the user cares for the pet. If the pet is not adequately "nourished," it may lose strength and its evolution into the characters can be inhibited.

Figure 10:
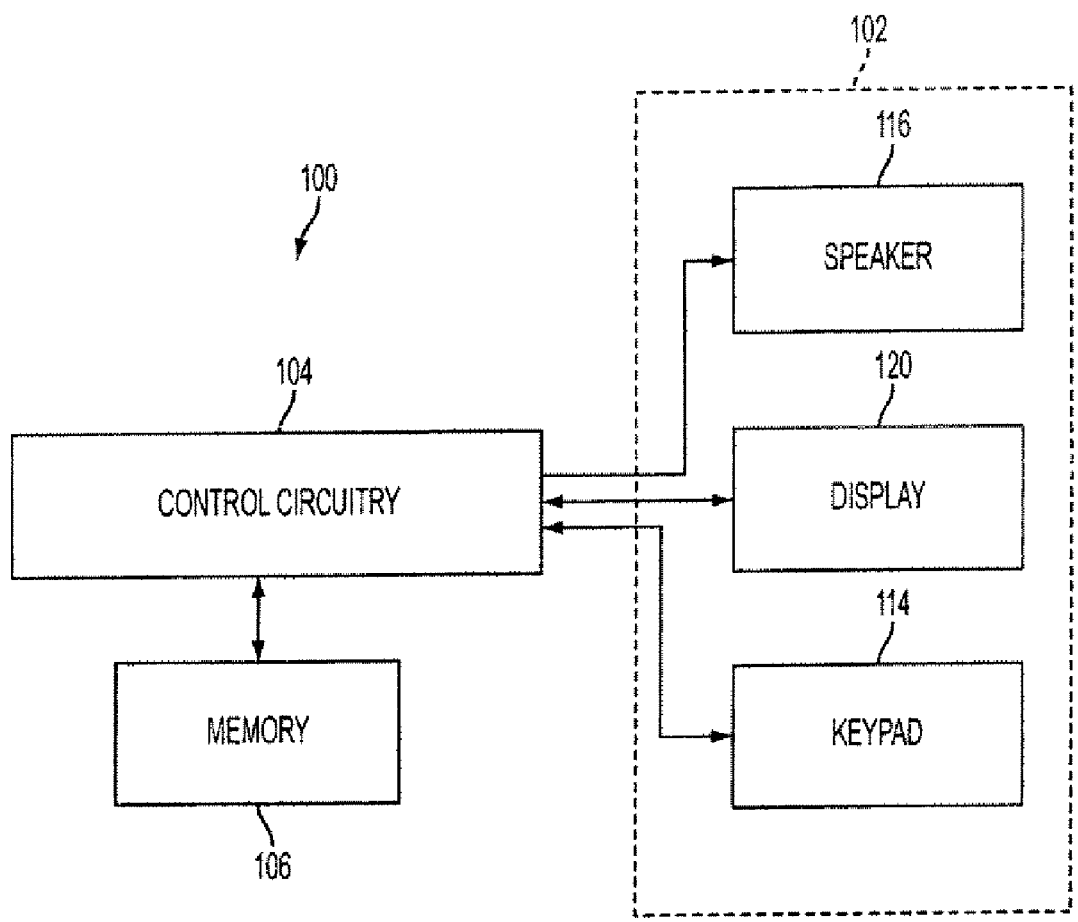
FIG. 10 is a schematic representation of a computing environment that can used with the toothbrush constructions.

FIG. 10 illustrates a schematic diagram of a general computing environment that can be used to implement various features described herein. In FIG. 10, a toothbrush 100 may include electronic components and application programs including a user interface 102, a control circuitry 104, and a memory 106. User interface 102 provides audio and/or visual signals to a user and enables a user to interact with the toothbrush electronic components. The user interface 102 is operatively connected to the control circuitry 104. The user interface 102 may optionally include a speaker display 116, a display device 120, and a keypad or button arrangement 114. The speaker device 116 provides audible signals to the user. The display device 120 provides visual signals to the user in the form of alphanumeric characters, colors or graphical symbols. The display device 120 may be a device used for computing devices, such as a liquid crystal display (LCD). The control circuitry 104 may include a microprocessor (not shown) for use with digital data. An interface circuit may include one or more wireless communication components such as an infrared LED and detector, and/or one or more antennas.

The control circuitry 104 is operatively coupled to memory 106. Memory 106 stores data installed or programmed by the user, including a game episode. Memory 106 may be any programmable type in which nonvolatile storage can be electrically erased and reprogrammed. Possible alternatives include flash memory, flash ROM, RAM with battery backup. It should be understood that a game episode formatted for toothbrush 100 may be downloaded to memory 106 or a game episode may be preloaded in the memory. The memory can be interchangeable with other types of devices, such as portable gaming devices, console systems, mobile telephones, personal digital assistants, personal computers, and the like, so that a game can be played (or continued) on a different device.

In one arrangement, memory 106 may be insertable in the control circuitry 104 so that various game programs can be interchangeably played with the same toothbrush. This embodiment memory 106 comprises a memory module with a housing, such as Compact Flash, Secure Digital Media, xSD, and the like. The handle 10 may have a slot for receiving and retaining an insertable memory module. In this way, toothbrush 1 provides an oral care platform for expansion of games and other programming related to or associated with oral care. Nevertheless, the games could have entertaining value unrelated to oral care.

The toothbrush 1 optionally can be provided with compartments and/or access panels for access to the various components, such as a power source. The power source can be, for example, a replaceable or rechargeable battery.

The handle 10 may be designed to enable the user to easily grip and manipulate the toothbrush. More particularly, the handle 10 may be shaped and/or include ergonomic features to provide a higher degree of control for the user while maintaining comfort. Examples of ergonomic features include an overmolded grip portion that can be segmented and ergonomically sized for users. The handle 10 may include sections that are angled relative to each other and/or which are wider or narrower than other portions of the handle to provide increased control and comfort during use. In the embodiment shown in FIGS. 8A and 8B, for example, a textured grip portion 31 can be provided to provide a non-slip surface for the user to grip the toothbrush. The grip portion 31 can be provided on the same side of the handle 10 as the bristles 16, on the opposite side of the handle 10 as the bristles 16, or around the circumference of the handle 10 as shown in FIGS. 8A and 8B. As shown in FIG. 8B, an elastomeric portion 31 also may be included on the side of the head 12 opposite the bristles 16, e.g., for aesthetic purposes or the like.

In one construction, an oral care implement can be equipped with operative features and structures/components to encourage social interaction between two or more individuals. The oral care implement provides an entertaining experience in which individuals compete against each other in a head-to-head competition. By encouraging social interaction between individuals, such as children, the overall oral care experience can be made more positive, which can help promote good oral care habits.

Figure 11:
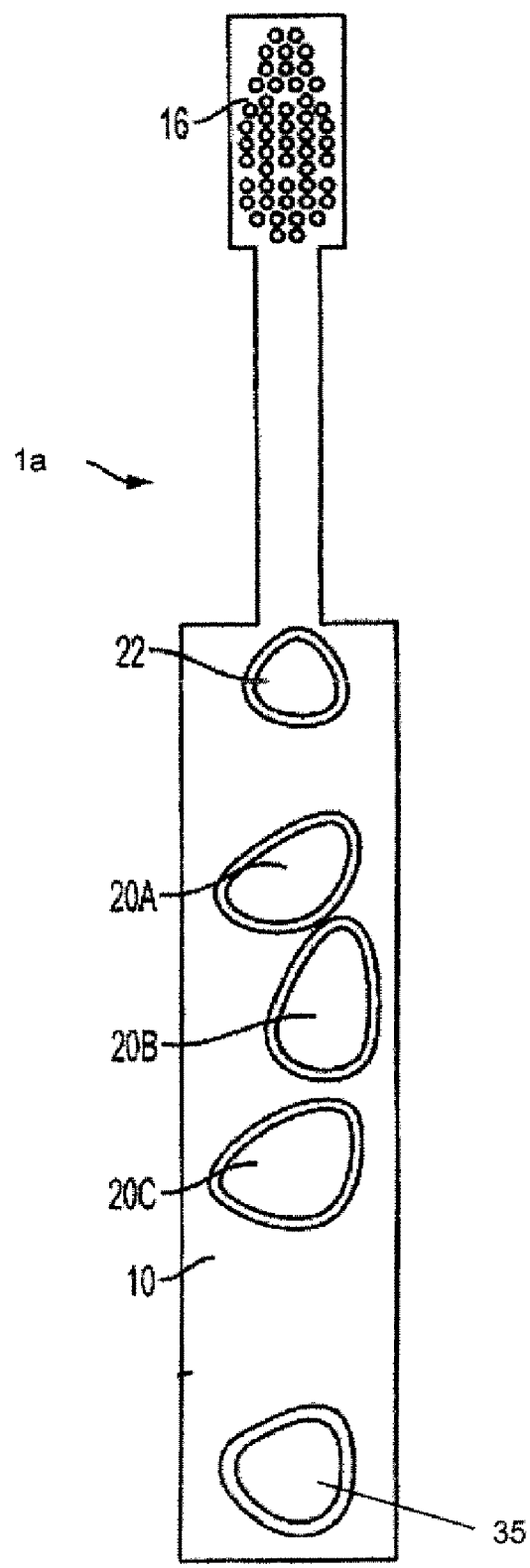
FIGS. 11 and 12 schematically illustrate a set of toothbrushes adapted for multiple users to play a game with one or more other users.
Figure 12:
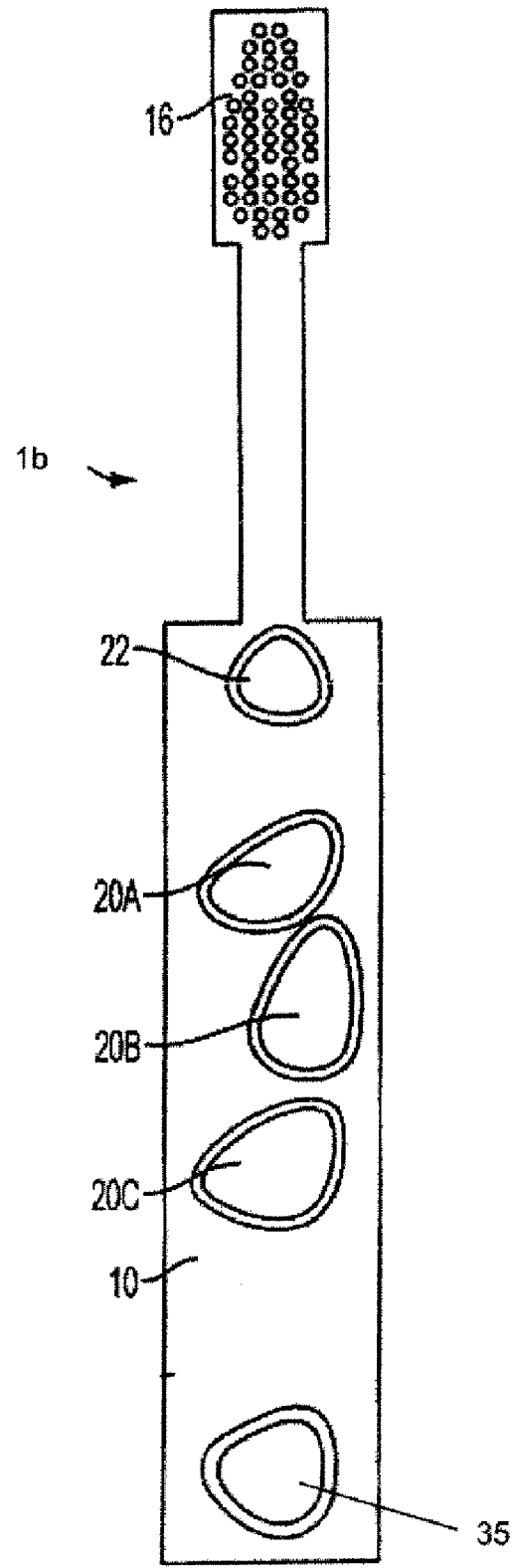

As an example of an oral care implement adapted to encourage social interaction, FIGS. 11 and 12 show a set of toothbrushes 100a and 100b which are adapted to enable two users to play an electronic game against each other. It should be understood that the toothbrushes 100a and 100b may include the features shown in FIGS. 10 and 13 pertaining to a general computing environment. The toothbrushes 100a and 100b can be adapted to communicate with each other wirelessly, such as by radio frequency signals, infrared signals, or the like.

Figure 13:
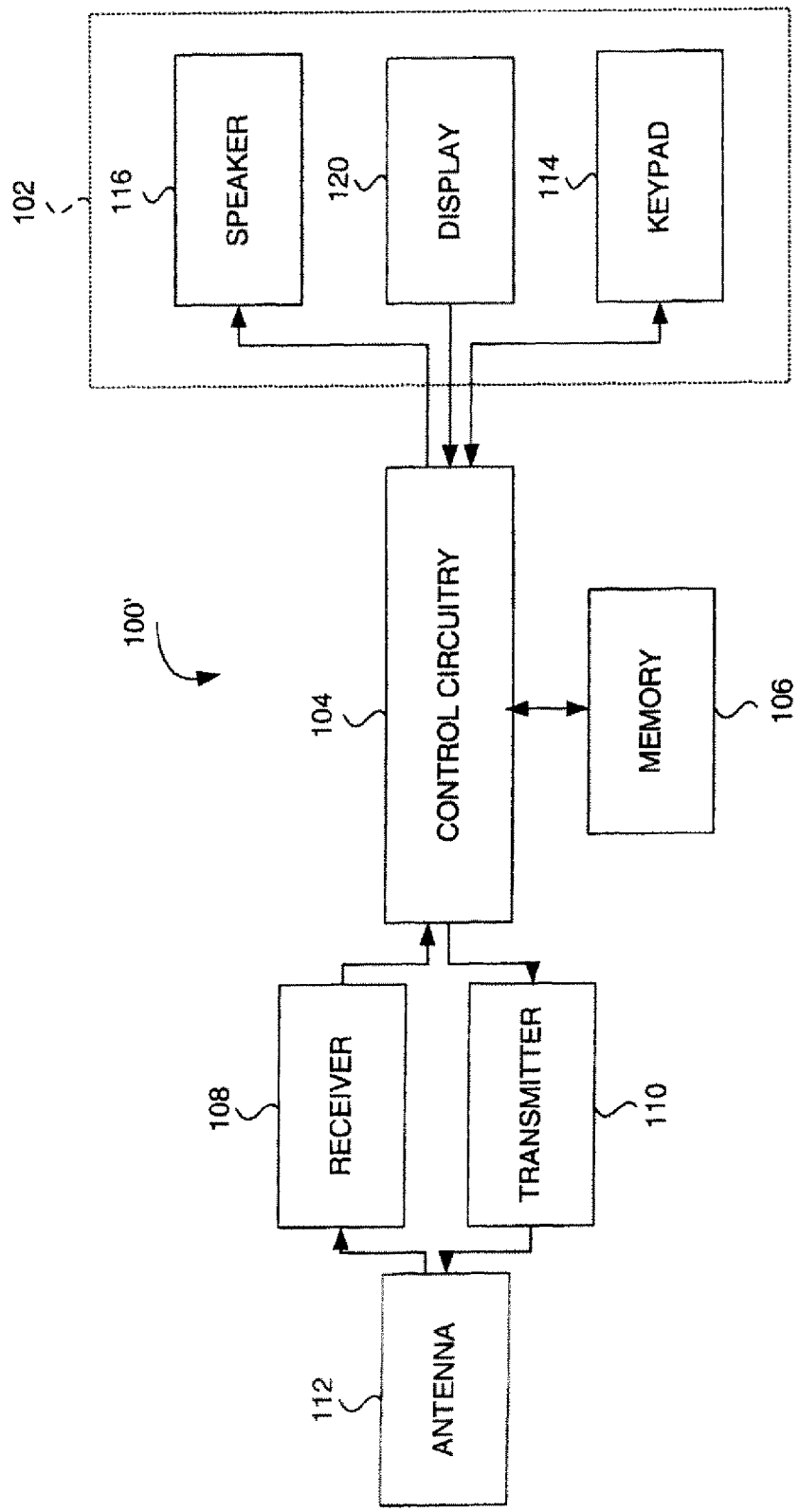
FIG. 13 is a schematic representation of an alternative computing environment that can used with the toothbrush constructions.

Referring to FIG. 13, the control circuitry 104 is further operatively coupled to a receiver 108, a transmitter 110 and antenna 112. The receiver 408 is operatively coupled to the antenna 412 for receiving a wireless communication payload, including data for a game episode. The transmitter 410 is also operatively coupled to the antenna 412 for sending a wireless communication payload, such as data between toothbrushes 100a and 100b.

The wireless connection provides the users with untethered freedom to use the toothbrushes for interactivity. For example, a wireless arrangement may include infrared frequencies or radio-controlled frequencies, such as Bluetooth radio-frequency ("RF") specification and protocols. One type of wireless connection may utilize widely available communication standards such as, the Infrared Data Association ("IrDA") specification and protocols, IrDA Data or IrDA Control. The IrDA communication protocols provide low-cost, short-range, cross-platform, point-to-point communications at various transfer rates for devices employing the standardized protocol. IrDA compatible hardware for transceivers and interfacing software modules are commercially available from various suppliers.

Alternatively, the wireless connection may be radio frequency based. The radio-controlled configuration may include a transmitter 108 and receiver 110 operating at 27 MHz, but other frequencies may be implemented. Further, it is contemplated that toothbrush 100a and 100b may have Wi-Fi capability such that it can communicate via a wireless network using 802.11b protocol. In yet another construction, toothbrush 100a and 100b may be ZIGBEE complaint devices. ZIGBEE pertains to an industry specification for a suite of communication protocols using small, low-power digital radio based on the IEEE 802.15.4 standard for wireless personal area networks which is incorporated by reference herein. The radio-controlled configuration may include a transmitter 108 and receiver 110 operating at 2.4 GHz, but other frequencies may be implemented in different geographic regions. The data transfer rates can be 250 Kbs, but other data rates slightly lower or higher could be used. Various commercially available ZIGBEE complaint modules could be implemented. Other known wireless transmission protocols or wireless medium arrangements also can be employed.

In another construction, the toothbrushes 100a and 100b may communicate with each in a wired arrangement, for example, using the Universal Serial Bus standard for data communications. In this example, the control circuitry may include the software to operate with the USB standard. The Universal Serial Bus can be the Universal Serial Bus-On-the-GO (USB-OTG) standard configured for portable device-to-device communications without a general purpose computer. This implementation is useful in that USB-OTG has low power consumption of about 8 milliamps to preserve the battery operating life. In an USB-OTG implementation, using a topology of host/peripheral, the control circuitry of toothbrush 100a may act as a host device and the other toothbrush 1b may act as a peripheral device. Alternatively, toothbrush 100b may act as the host and toothbrush 100a may act as a peripheral device. Further, data transfer with the USB-OTG protocol enables symmetric bi-directional communications between connected devices. Hence, data can be transferred and shared between the toothbrushes 100a and 100b. Nevertheless, other connection methods between the toothbrushes 100a and 100b are possible for data transfer.

With reference to FIGS. 11 and 12, toothbrushes 100a and 100b can be provided within a set and adapted to communicate with each other wirelessly by radio frequency signals, wired or the like as previously described. Nevertheless, more than two toothbrushes can be provided in a set. For ease of explanation the description will focus on two toothbrushes in a set. The set of toothbrushes 100a and 100b can be provided in which at least one of the toothbrushes 100a can be adapted to control features of one or more other toothbrushes (e.g., toothbrush 100b) in the set. Alternatively, toothbrush 100b could control one or more features of toothbrush 100a. In one construction, a kit may include a first oral care implement (e.g., toothbrush 100a) having a first user-interactive structure shown in FIG. 13, such as user interface 102, control circuitry 104, a receiver 108, a transmitter 110 and antenna 112, and a second oral care implement (e.g. toothbrush 100b) having a second user-interactive structure shown in FIG. 13. Toothbrush 100a and toothbrush 100b are adapted to communicate with each other by way of the first user-interactive structure receiving a signal from the second user-interactive structure.

In FIGS. 11 and 12, each of the toothbrushes 100a and 100b can be equipped with one or more computer implemented games. The game may include audio files and multimedia files encoded in computer readable format on a computer usable storage medium 106, such as programmable memory, or any other device that stores digital data for processing as shown in FIGS. 10 and 13. The audio files and multimedia files can be embodied in an appropriate digital encoded format for use in computing environments.

In one example of a computer implement game, toothbrushes 100a and 100b may include a game flow pertaining to "rock, paper, scissors". Each toothbrush 100a and 100b can have user input devices, such as buttons 20A, 20B, and 20C labeled with text and/or graphics depicting a rock, a paper, and a scissors. The toothbrushes 100a and 100b may have computer readable memories programmed with the rules of the game, namely (1) paper covers rock, (2) scissors cut paper, and (3) rock crushes scissors. The toothbrushes 100a and 100b are adapted to communicate with each other via a data connection to selectively engage the display or speaker to present indications/rewards to the users according to the rules of the game being played between the toothbrushes 100a and 100b.

In the example game play, when buttons are depressed on both toothbrushes 100a and 100b, a control circuit determines which toothbrush "wins" the game according to the above-described game flow rules. A "win" signal can be displayed and/or sounded on the "winning" toothbrush, and a "no-win" signal can be displayed and/or sounded on the other toothbrush. For example, a winning signal may comprise a blinking green light 35 and/or an upbeat melody. A no-win signal may comprise a blinking red light 35 (e.g. display engagement) and/or a tone (e.g., speaker engagement). A separate signal can be used, if desired, to indicate that both users selected the same button (for example an amber light and/or a distinctive melody). Further, each user may also receive points for win signal or points could be decremented for a no-win signal. Both the speaker and display can be used sequentially or simultaneously to indicate rewards/signals to the users of toothbrush 100a and toothbrush 100b.

The toothbrushes 100a and 100b can be adapted to enable individuals to play a wide variety of computer implemented games. Games described above with respect to FIGS. 1A-9B in the context of a single user, for example, can be adapted to be played by two or more individuals to encourage social interaction between the individuals.

Each toothbrush 100a and 100b can have a power button 22 to turn power on for itself as well as one or more additional toothbrushes within the set. When activated, a light 35 can be illuminated at the base of the handle of each toothbrush, for example, and the games can be enabled. The lights 35 and/or games can be disabled by depressing the power button 22 again, and/or a timing circuit can be provided to shut off power after non-use for a period of time.

Figure 14:
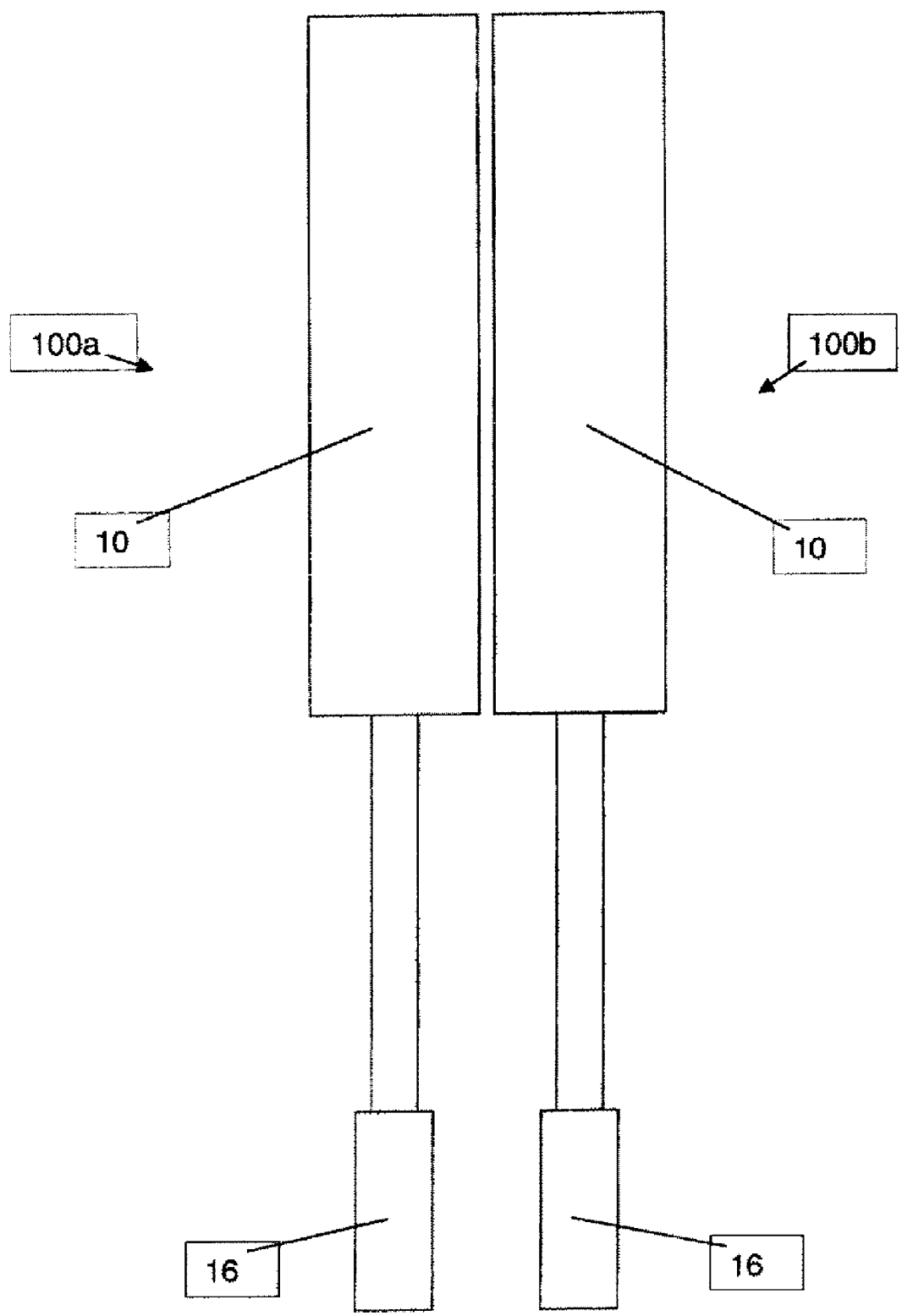
FIG. 14 is a schematic representation of packaging two or more toothbrushes together, which toothbrushes are adapted to enable a multiplicity of users to play an interactive game with one or more other users.

A set of toothbrushes 100a and 100b can be packaged together in a way that further encourages good oral care habits by making brushing a more pleasurable experience. For example, FIG. 14 is a schematic representation of packaging two or more toothbrushes 100a and 100b together. The toothbrushes 1a and 1b can be joined (for example by plastic molding which is easily separable) in a manner that resembles double halves. The two individuals can separate the halves and each take one half to share an interactive experience together. The toothbrushes 100a and 100b that are packaged together can have computer readable memories that are pre-programmed to enable two users to play a computer implemented game against each other, such as oral care games.

The handle and head sections can be molded from a plastic or resin such as polypropylene. Grip portions 31, buttons 20, 22, 30A, 30B, 30C, etc. and various other components of the toothbrush can be formed from elastomer materials well known to persons skilled in the art, such as propylene-ethylene copolymer elastomers. The elastomers can be incorporated using conventional molding techniques well known to those of ordinary skill, such as overmolding or co-injection molding techniques.

While the various features of the toothbrushes work together to achieve the advantages previously described, it is recognized that individual features and sub-combinations of these features can be used to obtain some of the aforementioned advantages without the necessity to adopt all of these features. It is understood that designations such as "first" and "second" are for illustrative purposes and can be interchanged.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein. While specific toothbrush configurations have been illustrated, the present invention is not limited to any of the aesthetic aspects shown and, in practice, may differ significantly from the illustrated configurations.

We claim:

1. A kit comprising:
   a first toothbrush having a first display and a first user interface to facilitate interaction with the first display;
   a second toothbrush having a second display and a second user interface to facilitate interaction with the second display; and
   wherein the first toothbrush and the second toothbrush are adapted to communicate with each other by way of: (1) the first toothbrush receiving a signal generated and transmitted by the second toothbrush that selectively activates the first display; and (2) the second toothbrush receiving a signal generated and transmitted by the first toothbrush that selectively activates the second display.

2. The kit of claim 1, wherein each of the first and second toothbrushes comprise a memory including computer readable instructions for operating a game.

3. The kit of claim 2, wherein each of the first and second toothbrushes includes a slot for receiving the memory therein.

4. The kit of claim 1, further comprising instructions for playing an interactive game with the first toothbrush and the second toothbrush.

5. The kit of claim 4 wherein the first toothbrush and the second toothbrush are releasably joined to each other.

6. The kit of claim 1, wherein the first and second toothbrushes are adapted to communicate with each other to present indications to users of the first and second toothbrushes according to rules of a game being played between the first and second toothbrushes.

7. A toothbrush, comprising:
   a head having cleaning elements;
   a handle including control circuitry;
   a display on the handle for illumination;
   a user interface on the handle to receive input for the control circuitry;
   the handle including communication circuitry coupled to the control circuitry, the communication circuitry comprising a receiver for receiving data from a second toothbrush and a transmitter for sending data from the toothbrush to the second toothbrush; and
   wherein the display is selectively activated by data received from the second toothbrush.

8. The toothbrush of claim 7, further comprising a memory for storing instructions associated with an oral care game.

9. The toothbrush of claim 8, wherein the game includes data responsive to said second toothbrush.

10. The toothbrush of claim 8, further comprising an opening in the handle configured to receive said memory, and wherein said memory is removable from said toothbrush.

11. The toothbrush of claim 7, wherein the toothbrush and the second toothbrush are adapted to communicate with each other to present indications to users of the toothbrush and the second toothbrush according to rules of a game being played between the toothbrush and the second toothbrush.

* * * * *